United States Patent [19]

Spinello

[11] Patent Number: 5,690,488
[45] Date of Patent: Nov. 25, 1997

[54] ANTI-SPLATTERING ROTARY DENTAL INSTRUMENT FOR CLEANING TEETH

[75] Inventor: Ronald P. Spinello, York, Pa.

[73] Assignee: Spintech, Inc., York, Pa.

[21] Appl. No.: 637,551

[22] Filed: Apr. 25, 1996

Related U.S. Application Data

[63] Continuation-in-part of Ser. No. 432,768, May 2, 1995, abandoned.

[51] Int. Cl.[6] .................. A61C 1/08; A61C 3/06
[52] U.S. Cl. .................. 433/116; 433/125; 433/166
[58] Field of Search .................. 433/116, 125, 433/166

[56] References Cited

U.S. PATENT DOCUMENTS

| | | | |
|---|---|---|---|
| 1,216,311 | 2/1917 | Hartman | 433/116 X |
| 1,834,726 | 12/1931 | Ozon | 433/116 |
| 2,707,329 | 5/1955 | Costoff | 433/166 |
| 2,943,343 | 7/1960 | Jankelson | 433/166 X |
| 4,266,933 | 5/1981 | Warden et al. | 433/125 X |
| 4,365,956 | 12/1982 | Bailey | 433/125 X |
| 4,424,036 | 1/1984 | Lokken | 433/116 |
| 5,131,846 | 7/1992 | Hall | 433/125 X |

*Primary Examiner*—Nicholas D. Lucchesi
*Attorney, Agent, or Firm*—Gottlieb, Rackman & Reisman

[57] ABSTRACT

A prophylactic dental apparatus is designed to minimize splatter from rotation of a rotating resilient element with a diverter which substantially surrounds at least a portion of the resilient element while affording full visibility to the operator of the instrument.

11 Claims, 4 Drawing Sheets

ANTI-SPLATTERING ROTARY DENTAL INSTRUMENT FOR CLEANING TEETH

RELATED APPLICATION DATA

This application is a continuation in part of U.S. patent application Ser. No. 08/432,768 filed on May 2, 1995, now abandoned.

This invention relates to dental instruments and more particularly to rotary prophylactic instruments for cleaning tooth surfaces.

BACKGROUND OF THE INVENTION

One of the most widely used prophylactic devices in the dental profession is known as a prophy angle. It is used to drive a small rotary, elastomeric cup at an angle to the handpiece and which, through an interface of abrasive slurry, is pressed resiliently against the tooth surfaces to effect the cleaning action. The slurry almost invariably entrains the patient's saliva to form an ever-enlarging ropey mass which migrates along the surfaces of the cup, from which it is flung randomly into the surrounding environment as contaminated splatter. Operating the instrument in the critical gingival spaces under the margins of the gums adds blood pathogens to the slurry, raising the level of contamination of the splatter. The endangered contamination area associated with the use of prophy angles has been quantified as an ellipse approximately 48 inches wide and 30 inches high, which includes much of the dental chair, its support equipment and, of course, the professional personnel.

THE PRIOR ART

The prior art discloses three basic techniques for controlling splatter from rotary elastomeric cleaning cups: (1) shields to catch the splatter after it is hurled from the whirling cup as shown in U.S. Pat. Nos. 1,834,726, 4,424,036 and 5,131,846; (2) impellers or vanes formed on the cup surfaces to direct the slurry away from the surfaces from which the slurry is most likely to be thrown, as shown in U.S. Pat. Nos. 5,131,846, 4,259,071 and 3,727,315; and (3) wiper arms adapted to engage the rotary cups to intercept the migration of the slurry before it reaches the critical areas of the cup from which it will be splattered into the environment, as shown in U.S. Pat. Nos. 3,727,315 and 2,943,343.

There are problems with all of the three splatter control systems previously proposed which have discouraged their adaption and use. External, splatter-catching shields impair vision of the cleaning site and interfere with the ability of the tool to reach critical tooth surfaces. Also, shields which engage the rotary cup cause friction which in the presence of the abrasive slurry causes heating and self-destruction of the cup. Impellers or vanes tend to preclude essential bi-directional rotation of the cup, and also have limited efficacy to control slurry migration. Wiper arms either interfere with the essential cup flexing action or fail to maintain contact at critical times. Also, such contact generates friction, similar to that of flexible stationary shields, and heating and self-destruction of the cup results.

SUMMARY OF THE INVENTION

The present invention is based on the discovery that it is possible to control splatter for both directions of cup rotation without frictional contact with the cup and without impairing the dentist's vision. The invention identifies a heretofore unrecognized critical point on the rotary cup where the axially migrating slurry, which is rotating with the cups, can be intercepted adjacent the base of the cup without frictional engagement with the cup. When intercepted, the rotating motion of the slurry is damped to eliminate its dynamic forces before the radially enlarged masses can build up to be thrown off by centrifugal force, thus causing it to be diverted harmlessly away in a direction which depends on the position of the instrument.

In accordance with the invention a thin-walled circular diverter or diffuser closely surrounds the base at the proximal end of the cup closely adjacent the point at which the cup flares outward when pressed against the tooth. In some cup designs, there is a necked down portion between the base and the flaring portion to augment the flexing action and it is preferred to place the working edge of the diverter very close to the point at which the necked down portion merges into the base. A preferred geometry for the circular diverter is a stationary thin-walled cylindrical sleeve carried by the housing of the prophy angle and which closely surrounds but does not touch the base of the rotating cup. The outer edge of the sleeve is disposed close to the point at which the base of the cup merges into the flaring or flexing portion. Extending the sleeve significantly further can impair vision, interfere with the critical flexing action, and create pockets in which flesh can be nipped.

Another feature of this invention is its ability to control the migration of the contaminated abrasive slurry in the narrow toroidal clearance space between the base of the cup and the cylindrical diverter sleeve. Depending on the design of the prophy angle, the slurry can migrate into the gear chamber to cause overheating capable of burning the patient as well as premature destruction of the gears. In accordance with the invention, this migration, as well as other external flow patterns of the slurry, can be controlled by providing apertures in the cylindrical sleeve which are critically located and sized so that they do not themselves become paths for centrifugally impelled splatter.

DETAILED DESCRIPTION

Figure 1:
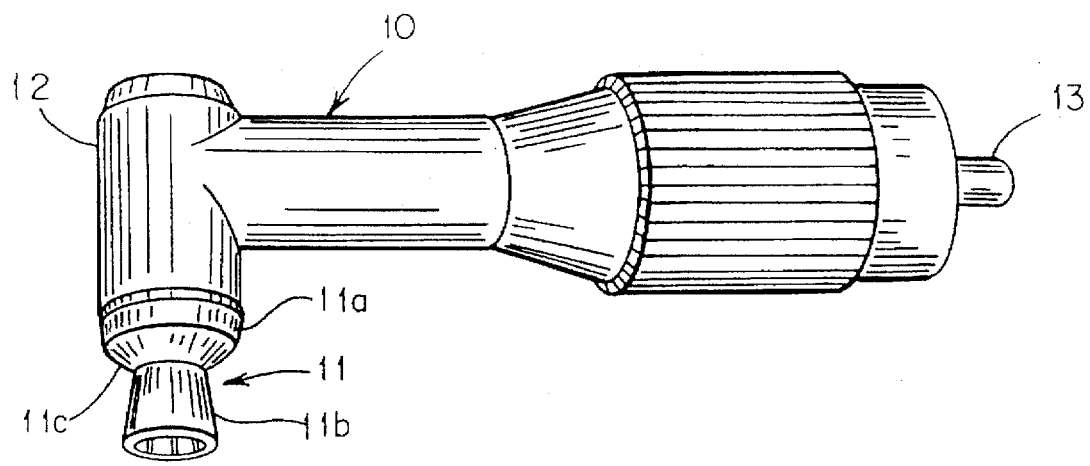
FIG. 1 is a view in perspective showing a rotary dental cleaning instrument, known as a prophy angle, of conventional design.

Referring to FIG. 1, there is shown in enlarged scale a conventional dental instrument 10 commonly known as a prophy angle which attaches to a conventional hand piece driver (not shown) such as an air driven rotor. The prophy angle 10 carries a disposable elastomeric cup portion 11 having a base 11a which is detachably secured to an axle (not shown) in a housing 12 having gears and bearings (not shown) to convert the rotation of its input shaft 13 to rotation at an angle, typically ranging from 45° to 90° (the latter as shown), to the hand piece.

The working end or cleaning head 11b of the cup portion 11 is adapted to flare outwardly when pressed against a tooth surface in the presence of an abrasive slurry to remove deposits and stains from the tooth surface. In the illustrated cup portion 11, a necked-down center section 11c is formed between the base 11a and the flexible cleaning head 11b to facilitate the flaring action. Cup portions 11 are furnished to the profession in a range of different geometries and flexing characteristics but the generally cylindrical base portion 11a by means of which they are detachably mounted on the prophy angle are of more or less similar shapes. Prophy angles are now designed to be disposable after one use in a profession-wide endeavor to eliminate all sources of cross-contamination.

Figure 1A:
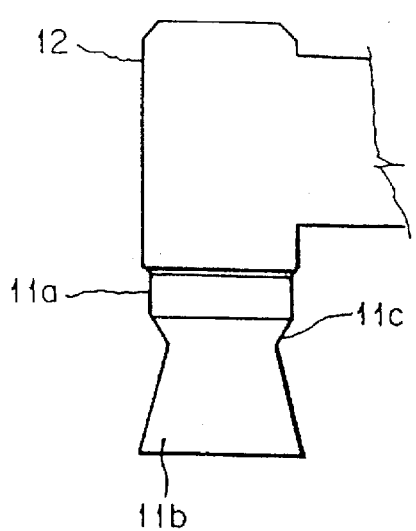
FIG. 1A is a side view in enlarged scale of the head end of the instrument in FIG. 1.
Figure 1B:
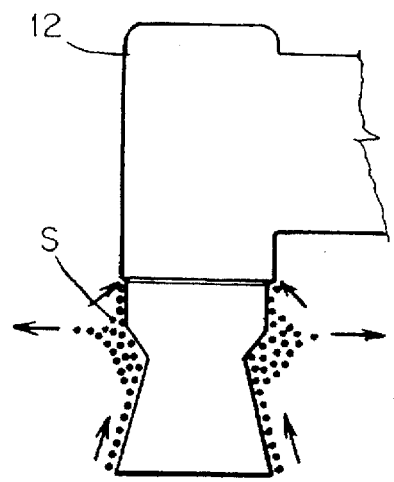
FIG. 1B is a side view showing diagrammatically the action of the conventional instrument of FIG. 1 in the presence of saliva-contaminated abrasive slurry.

A remaining and flagrant source of potential contamination in the dental profession, however, is the splatter of the abrasive slurry, entraining saliva and blood pathogens from the patient, which is thrown into the environment at the dental chair by the spinning cup of the prophy angle. The principal source of this splatter is illustrated in FIGS. 1A and 1B in which the working end of the prophy angle is shown in enlarged scale. In operation, the dentist typically dips the flexible working end 11b of the elastomeric cleaning portion 11 into an abrasive slurry to be pressed against the tooth before rotation is begun. It will be understood that the working end 11b, being hollow, will splay outwardly to bring the internal surface hard against the tooth surface. As the procedure continues, varying pressures are applied to the instrument at varying speeds of rotation and flexing is more or less continuous. Some slurry will be urged by the centrifugal force of the rapid rotation from the flared outer edges but the dynamics of this flow will be substantially arrested by the stationary tooth surface over which the flow occurs. Meantime, the patient's saliva becomes entrained in the slurry, imparting additional mass and also changing the surface tension and viscosity of the mixture. Referring to FIG. 1B, some of this material will appear on the outer surfaces of the cup portion to begin, when the instrument is pressed against the tooth surfaces, an inexorable migration inwardly and upwardly along the outside wall of the cup. Reaching the base portion 11a, the saliva and abrasive slurry mass S builds to the point at which centrifugal forces overcome all offsetting forces and splatter results.

Figure 2:
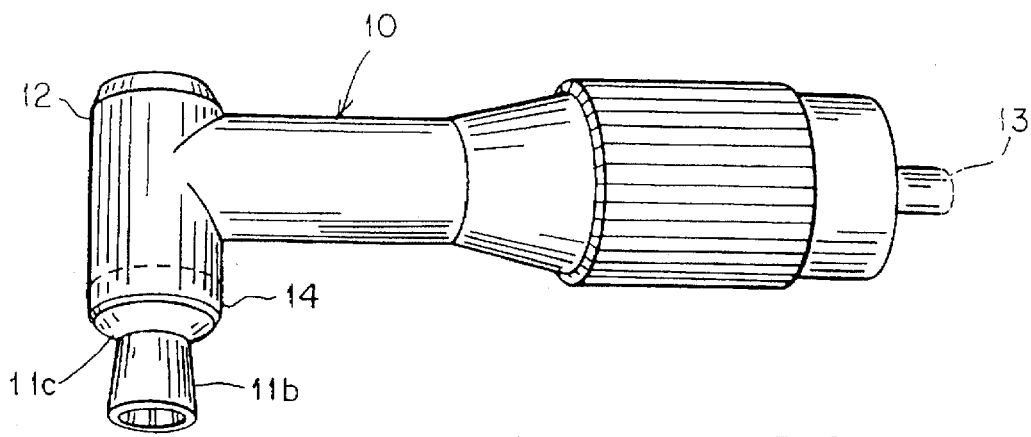
FIG. 2 is a view corresponding to FIG. 1 showing one embodiment of the present invention.

In accordance with the invention, splattering from the cup portion 11 can be substantially reduced by means of a stationary, circular diverter 14 (FIGS. 2, 2A and 2B) carried by the housing 12 and taking, in one preferred form, the shape of a thin-walled cylindrical sleeve which closely surrounds but does not touch the base 11a of a cup portion 11. The base 11a of the elastomeric cup 11 is capable of bulging radially under both the centrifugal forces of high speed rotation and the axial compression forces placed on the cup when it is forced against a tooth. Clearance should be provided between the deflector and the cup base to accommodate this deformation of the cup. In one preferred embodiment of the invention, clearances in the range of about 0.25–1.5 mm are effective to both accommodate cup deformation and preclude splatter.

Figures 2A, 2B:
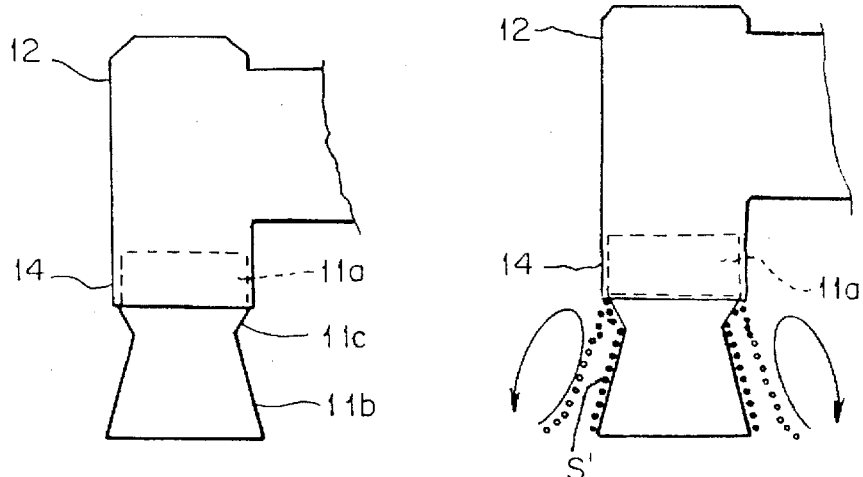
FIG. 2A is a side view in enlarged scale of the head or distal end of the instrument of FIG. 2 showing this embodiment of the present invention.
FIG. 2B is a side view showing diagrammatically the action of the present invention in the presence of saliva-contaminated abrasive slurry.

In the illustrated form, the circular diverter 14 has its lower edge terminating adjacent the line of merger of the necked-down, central portion 11c with the base 11a. At this point, the diverter 14 intercepts and damps the high speed rotary component of the axially migrating slurry S', as best seen in FIG. 2B, before any substantial mass can build up. Sapped of its high speed rotary component, the slurry will not detach as splatter but, depending on the attitude of the instrument, will drain back toward the tooth or harmlessly over the housing 12. There is some tolerance as to the extension of the circular diverter 14 further toward the flarable head portion 11b although the diverter should not block the dentist's view of the tooth surface and should not frictionally engage the flaring portion of the cup.

Figure 3:
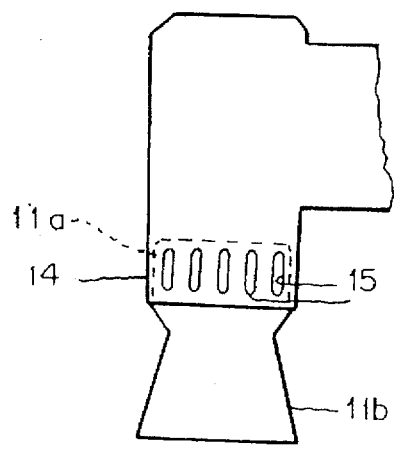
FIG. 3 is a side view of the head portion of a dental cleaning instrument showing another embodiment of the invention.
Figure 4:
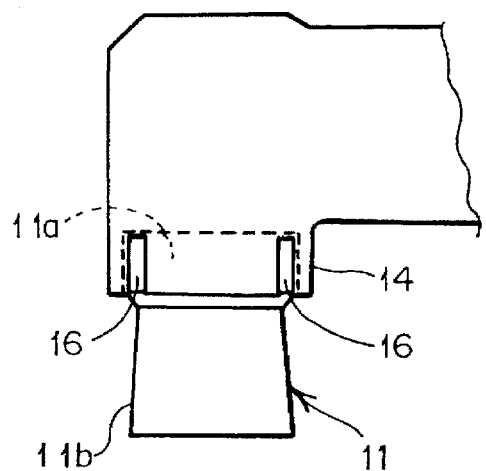
FIG. 4 is a side view of another embodiment of the invention.
Figure 7:
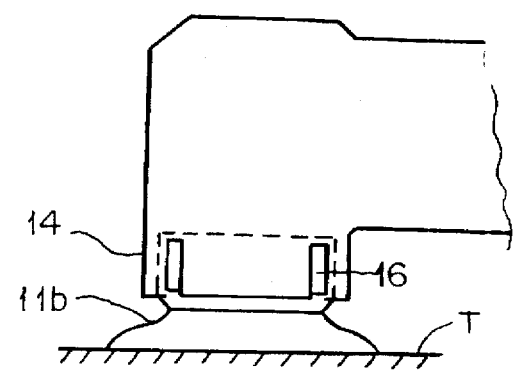
FIG. 7 is a side view of a prophy angle of the embodiment of FIGS. 4-6 pressed against a tooth surface.
Figure 5:
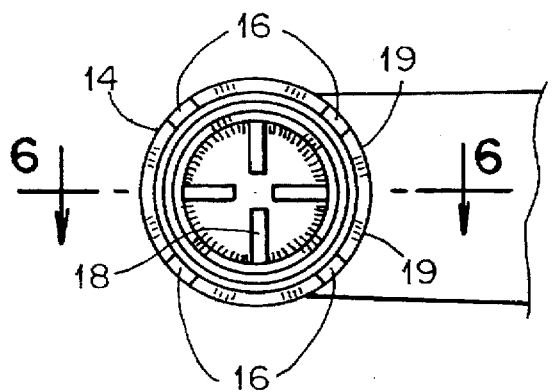
FIG. 5 is a bottom view of the prophy angle of FIG. 4 showing the working end of the cup.

The invention also provides for the control of the migration of the slurry within the closely controlled toroidal space between the wall of the cylindrical base 11a and the inner wall of the cylindrical diverter 14. In accordance with the present invention, the forces which induce this portion of the migration path can be substantially reduced by providing apertures 15 in the stationary cylindrical diverter 14, as best seen in FIG. 3.

The apertures 15 are shown in the form of an array of relatively narrow, axial slots which provide for pressure and flow control within the toroidal space to arrest the migration of the slurry into the housings 12 where it can cause damage to the gearing including internal heating capable of burning a patient's mouth. The ratio of the aperture area to diverter wall area must be kept sufficiently low to preclude exposure of the rotating surface of the cup base 11a in amounts sufficient to pass splatter. The size must also be kept small to preclude the possibility of flesh such as cheek lining being grabbed between the rotating surfaces of the cup 11 and the stationary edges of the diverter 14.

Figure 6:
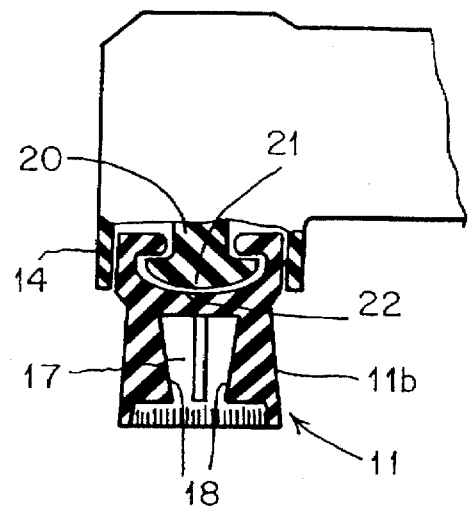
FIG. 6 is a view in partial cross-section taken on the line 6—6 of FIG. 5.

Referring to FIGS. 4–7, there is illustrated another embodiment of the invention in which the circular diverter or skirt 14 is formed with four open-ended slots 16 spaced apart at approximately 90° intervals around the circumference. As best seen in FIG. 6 the diverter skirt 14 is extended to a point slightly below the cylindrical base portion 11a of the cup 11. As described above and as illustrated in FIG. 7, the cup 11 is designed to flare or splay outwardly when pressed against a tooth surface T. The hollow interior 17 of the cup contains typical cleaning and polishing patterns such as raised ribs 18 and striations 19 of which there are many designs in the art. The cup is driven by a rotary shaft 20 having an attaching knob 21 which snaps snugly into an opening 22 in the cylindrical base, all as conventional in the art. The slots 16 relieve the pressure of the polishing compound or paste within the toroidal space between the rotating cup 11 and the inside diameter of the circular diverter skirt 14.

There is a range of spacing tolerances for the toroidal space depending on a number of design and material characteristics, including resiliency of the cup, slot locations, manufacturing tolerances and the like. Useful operational results have been measured with clearances ranging from approximately 1.5 millimeters down to approximately 0.25 millimeters. In general, smaller clearances can be used with the embodiments of the invention, particularly those shown in FIGS. 9–12 because of the conical configuration of the base of the cup, all as described below. The clearance between the diverter and the cup should be sufficient to prevent rubbing of the cup on the diverter wall when the rotating cup is pressed against the tooth.

Figure 9:
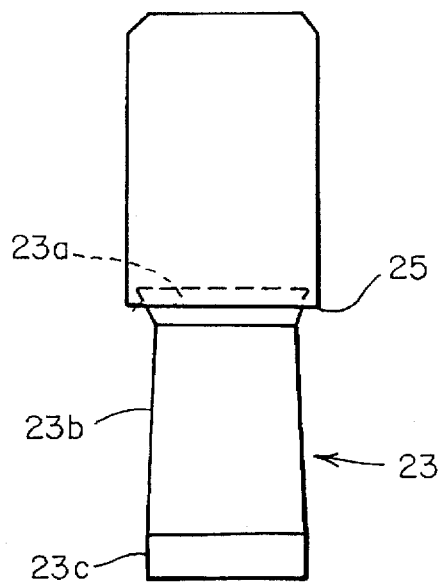
FIGS. 9, 10 & 11 are side views of the prophy angle of FIG. 8 showing, respectively, three different embodiments of the invention applied thereto.
Figure 10:
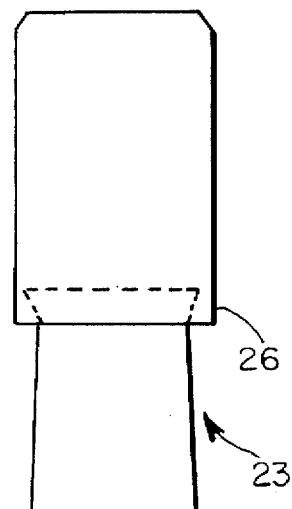
Figure 8:
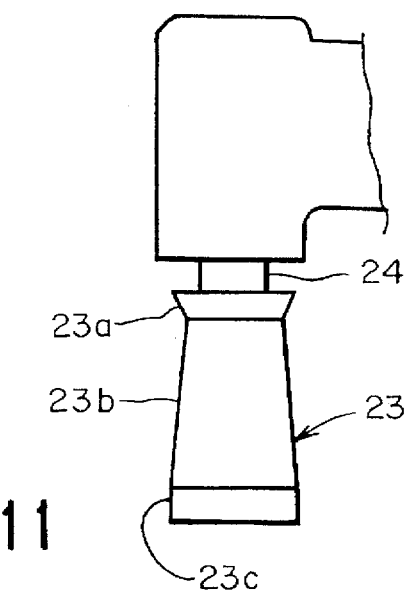
FIG. 8 is a side view of prior art prophy angle.
Figure 11:
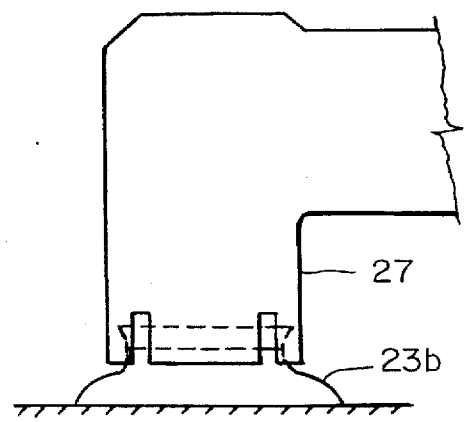

Referring to FIGS. 9–11, embodiments of the present invention are illustrated in combination with another prior art polishing and cleaning cup 23. Shown in FIG. 8 is a prior art polishing cup 23 in which the base portion 23a is the frustum of a cone convergent toward the hollow, flarable, working or head end of the cup, the latter comprising a divergent, elongated, frusto conical central section 23b and a short, generally cylindrical head portion 23c. The cup 23 is driven by a rotary shaft 24 attached to the base portion 23a and driven by conventional gearing.

As shown in FIG. 9, the base portion 23a is partially surrounded, in accordance with the invention by a circular diverter skirt 25. In this embodiment the diverter eclipses a portion of the base 23a having the largest diameter but does not extend to divergent section 23b.

The embodiment of FIG. 10 shows a diverter 26 which eclipses substantially the entire base portion 23a and terminates at or very close to the boundary of convergent portion 23a and divergent portion 23b. The diverter 27 of FIG. 11 is shown as eclipsing, in addition to the convergent base portion 23a, a portion of the central divergent section 23b. In FIG. 11 the cup is shown pressed against a tooth surface T and the extended diverter skirt is dimensioned to be disposed very close to but not touching the surface of the flattened cup portion 23b.

Figure 12:
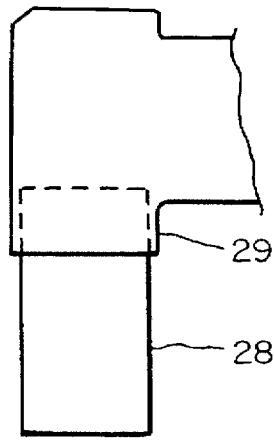
FIG. 12 is a side view of a prophy angle showing the invention applied to another prior art polishing cup design.

Referring to FIG. 12, another embodiment of the present invention is illustrated as applied to a prophy angle having a cup 28 which is substantially cylindrical. In this embodiment the circular diverter skirt 29 extends downwardly to eclipse a section of the cup for a distance which will prevent the diverter from engaging the cup when flared against a tooth surface but close enough to intercept the slurry of migrating material, which spins with the cup, before it is thrown off as splatter, and to dampen its rotary component in accordance with the invention.

While the invention has been described having references to preferred embodiments, it will be understood that it can take other forms and arrangements. For example, a series of circumferentially spaced circular holes can be substituted for the aperture pattern 15 in FIG. 3. Also, the means by which the circular diverter 14 is attached to the housing 12 can be varied. Rather than being formed as an integrated, unitary extension of the housing, it can be attached as a separate element. Also, brushes have in the past been used as the rotary cup elements and such should be regarded as substantially equivalent to elastomeric cups. The invention should not, therefore, be regarded as limited except as defined in the following claims.

What is claimed is:

1. A splatter resistant prophylactic dental apparatus comprising:

a rotatable tooth-cleaning element comprising a resilient, radially-flarable tooth-engaging head portion and a base portion to carry said head portion;

a housing to carry said tooth-cleaning element; and means for diverting splatterable migrating slurries on the rotatable element before they detach therefrom by centrifugal force as splatter, said diverting means closely surrounding at least a portion of said base portion of said tooth-cleaning element to define a narrow gap therebetween;

said base portion is sufficiently rigid to preclude contact with the diverting means during rotation;

the forward end of said diverting means terminating at a point which affords an open view of the radially flarable head portion but precludes engagement therewith both in its flared working configuration and in its unflared non-working configuration;

whereby the diverting means is positioned to engage slurries which migrate on the outer surface during rotation of the tooth-cleaning element without touching the element to damp the rotational momentum of the slurry before accumulations thereof are hurled into the surrounding environment as contaminated splatter.

2. A splatter resistant prophylactic dental apparatus as set forth in claim 1 wherein said rotatable element comprises a necked down portion between the head portion and the base portion.

3. A splatter-resistant prophylactic dental apparatus as set forth in claim 2 wherein said base portion is substantially cylindrical and said diverting means extends as forwardly as the necked down portion.

4. A splatter-resistant prophylactic dental apparatus as set forth in claim 1 wherein said base portion comprises an outwardly convergent wall to define a section of a cone;

said head portion comprises an outwardly divergent wall to define a section of a cone; and said diverting means comprises a forward end terminating at a point between the inner end of the convergent wall of the base portion and an inner end of the divergent wall of the head portion.

5. A splatter-resistant prophylactic dental apparatus as set forth in claim 1 wherein said diverting means comprises a substantially cylindrical sleeve.

6. A splatter-resistant prophylactic dental apparatus as set forth in claim 1 wherein said diverting means comprises apertures to vent said narrow gap and to reduce pressure and provide flow paths for accumulated momentum-damped slurry.

7. A splatter resistant prophylactic dental apparatus as set forth in claim 1 wherein said narrow gap has a range of sizes from approximately 0.25 mm to 1.5 mm.

8. A splatter resistant prophylactic dental apparatus as set forth in claim 7, wherein said diverting means is substantially cylindrical, and comprises apertures.

9. A splatter resistant prophylactic dental apparatus as set forth in claim 8, wherein said apertures are circumferentially spaced, axially elongated slots.

10. A splatter resistant prophylactic dental apparatus as set forth in claim 9, said apertures are open ended at the outer end of the diverting means.

11. A method of dental prophylaxis comprising the steps of:

pressing a radially flarable resilient, rotary element against a tooth surface in the presence of a slurry comprising an abrasive and the patient's saliva; thereby creating migrations of the slurry along the outer surface of the rotary element having a tendency to accumulate and be hurled into the surrounding environment; and intercepting the migrating slurry without touching the rotary element while it is on the rotary element before said slurry reaches the outer end of the rotary element to damp the rotational momentum of the slurry before accumulations of the slurry can be hurled into the surrounding environment as contaminated splatter, the point of interception being sufficiently high on the wall of the rotary element to afford an open view of the flarable, working end of the rotary element.

* * * * *